United States Patent [19]

Curtis et al.

[11] Patent Number: 4,509,530
[45] Date of Patent: Apr. 9, 1985

[54] SYSTEM FOR PLOTTING A MINIATURE ECG

[75] Inventors: Huntington W. Curtis, Chelsea; Frederick A. Dodge, Katonah; David B. Francis, Mt. Kisco; John V. Mizzi, Poughkeepsie, all of N.Y.

[73] Assignee: International Business Machines Corporation, Armonk, N.Y.

[21] Appl. No.: 565,499

[22] Filed: Dec. 27, 1983

[51] Int. Cl.³ .............................................. A61B 5/04
[52] U.S. Cl. ............................... 128/710; 346/33 ME
[58] Field of Search ............................... 128/702-704, 128/710; 346/33 ME

[56] References Cited

U.S. PATENT DOCUMENTS

| | | | |
|---|---|---|---|
| 3,087,488 | 4/1963 | Streimer | 346/33 ME |
| 3,221,334 | 11/1965 | Jones, Jr. | 346/33 ME |
| 3,909,792 | 9/1975 | Harris et al. | 128/702 |
| 4,051,482 | 9/1977 | Andresen | 128/710 |
| 4,068,310 | 1/1978 | Friauf | 128/710 |
| 4,109,243 | 8/1978 | Day et al. | 128/710 |
| 4,119,090 | 10/1978 | Dehnert | 346/33 ME |

Primary Examiner—William E. Kamm
Attorney, Agent, or Firm—Sughrue, Mion, Zinn, Macpeak, and Seas

[57] ABSTRACT

A method of printing an analog waveform having a time variable, such as an ECG by first converting the analog waveform into a time sequence of digitally expressed values, forming predetermined groups of digital data and then determining maximum and minimum amplitude values of the digital data within the groups. These values are stored in a line buffer memory. A recording medium advances past a transversely oriented linear array of discrete recording elements, such as a linear array dot printhead. The serial stored values are read out in parallel to each of the recording elements, with the elements actuated in parallel by the stored values at an initial time and for time durations for each element that is a function of the stored maximum and minimum amplitude values for that element. The waveform is recorded as a series of appropriately placed short parallel longitudinal lines to form in aggregate a transverse waveform display on the recording medium.

13 Claims, 8 Drawing Figures

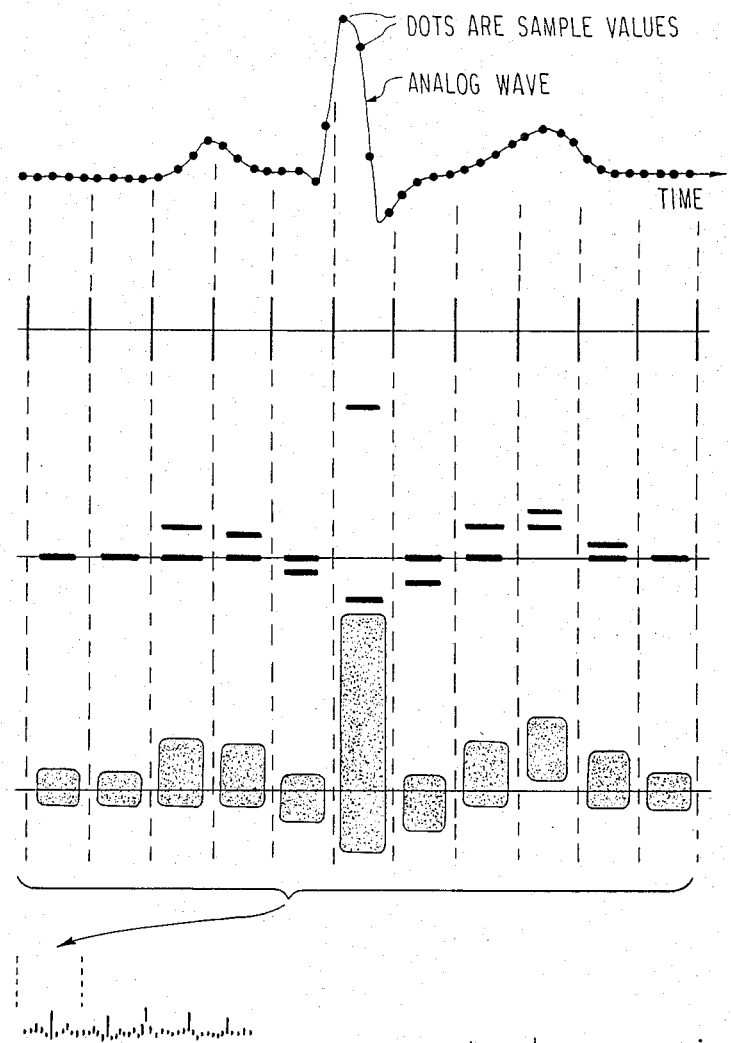
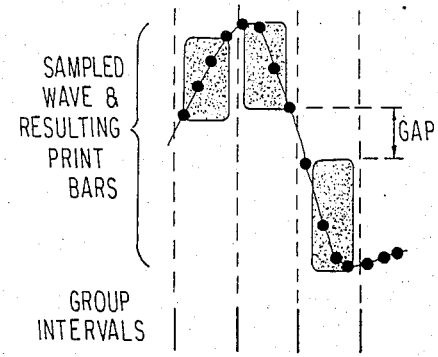
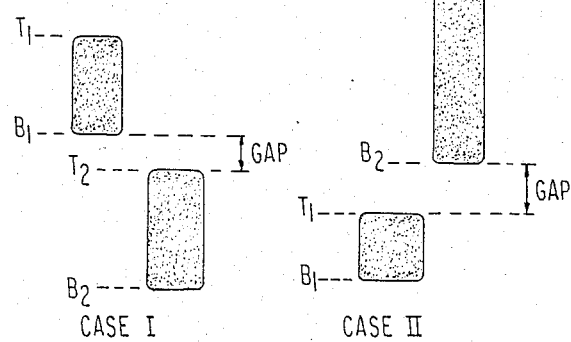

SYSTEM FOR PLOTTING A MINIATURE ECG

BACKGROUND OF THE INVENTION

Field of the Invention

This invention relates to a system of data recording, and in particular to a system for plotting a highly space-compressed train of electrocardiograph (ECG) waveforms, here termed a miniature ECG.

Systems for utilizing electrocardiograph signals for various display purposes are well known in the technology. Typically, with the subject in a resting state, data signals are received for a duration of only a few minutes and are then recorded on strip chart form for diagnosis. Other techniques employ long term heart monitoring and subsequent graphical recording of ECG signals for other diagnostic purposes. For example, long term monitoring allows a diagnostician to evaluate transient cardiac abnormalities which may be represented in the ECG of an ambulatory person as he conducts his daily business. The person will carry a tape recorder receiving ECG data from sensors affixed to the person. At a later point in time the tape is converted into a visible record and the ECG correlated to activity of the person. The amount of data accumulated is very large. U.S. Pat. No. 4,214,590 describes a technique of recording ECG signals onto tape and then transcribing that data onto hard copies in a compressed format. The recording per se utilizes a conventional endless loop with stylii controlled by galvanometers to perform the actual tracing. Thus, as shown in FIG. 3 of the '590 reference, tracing proceeds along an axis parallel to the direction of movement of the paper. The time axis is the direction of paper movement.

Techniques of data compression to eliminate redundant data in ECG systems is recognized in U.S. Pat. No. 4,090,505. As described therein, a reduction in redundant data is achieved while preserving random or infrequent occurring phenomena which may not normally be observed. Thus, variations in rhythm, that is arrhythmias which are detected by observing the resulting atypical waveforms or aberrations in the electrocardiogram tracing that are preserved. At the same time, the overall volume of electrocardiographic data is reduced in size such that a sufficient amount of routine data is preserved for comparison while at the same time all atypical data is displayed. Thus, by a technique of data compression which eliminates redundant data a medically acceptable electrocardiogram of greatly reduced size is achieved. The output occurs on a normal chart strip recorder having a standard resolution. That is, the dimension of the chart parallel to the direction of movement displays time relationships. Chart speed is in the range of 25 mm/sec with the stylus having the ability to denote of the order of ±2.5 millivolts of heart electrical activity. Consequently, the '505 reference utilizes a standard graphical output of electrocardiographic data, albeit eliminating that which appears to be redundant.

Other techniques of data compression, while not having specific application to ECG technology are known. For example, U.S. Pat. No. 4,109,243 describes a technique of storing data that would otherwise be lost during the retrace-blanking in a CRT scan. Data is plotted on a compressed time scale during the normal scan phase. The system therefore produces time compression by utilizing a recirculating memory storage for the temporary storage of input data followed by reading in a serial output, time compressed form. These techniques are not applicable to ECG plotting wherein continuous tracing takes place.

Other techniques deal with CRT plotting implementation where there is a difference between plotting resolution and the accuracy of the data base. U.S. Pat. No. 4,074,281 is representative of such technology employing line segment generation of multi-value time functions. Other references considered vis-a-vis the issue of CRT display or, generally the concept of data display systems, are represented in U.S. Pat. Nos. 3,680,076; 3,686,662; 3,812,491; and 3,902,476. None of those techniques are germane to data compression of ECG data.

While data collection and display technology has focused on the problem of accurate representation of voluminous, repetitious ECG data, there also exists a requirement to significantly simplify not only the data output but the equipment used to provide that pictorial record. Additionally, for some applications, high resolution is not necessary. For example, in the case of an ambulatory ECG system only gross variations in waveform need to be initially identified. Detailed analysis of the P, Q, R, S, T portions of a heart cycle waveform can take place after an arrhythmia has been identified. The use of precise ECG instruments for high resolution plotting is inconsistent with the initial use of ambulatory data. Such high resolution plotting is also costly and time consuming. Consequently, for this application, if all data is displayed in compressed format, arrhythmias are not lost in data compression. Thus, while low resolution data recording takes place for initial screening, the output is satisfactory. The problem to be addressed is both to reduce the volume of the printed record and to employ adequately precise (but much more rapid and less costly) plotting equipment compared to current high resolution ECG plotting methods.

Many existing diagnostic ECG systems rely on galvanometer technology utilizing a movable pen stylus and precise paper handling apparatus. Such are required, for example, as recognized in U.S. Pat. Nos. 4,090,505 and 4,184,487 for the purpose of obtaining an accurate standardized tracing. However, if accurate, high resolution is not required, alternative printhead technology, for example a thermal printhead utilizing a linear dot array, may be utilized. Such printheads are employed in some conventional computer output devices, and require a thermally sensitive recording medium. (Similar linear dot array printhead technology uses spark/arc "writing" via electroerosion or chemical action on an appropriately prepared recording medium.)

However, even if this equipment is used there is a requirement to provide for a significant amount of data compression to take place. For example, printing high resolution diagnostic electrocardiogram waveforms conventionally takes place using the direction of paper movement as the time axis. Thus, in applications where a low resolution is acceptable, i.e., ambulatory ECG's, significant reductions in paper output are still not achieved by merely replacing conventional galvanometer stylus recorders with an alternative printhead technology.

The principal advantage of the thermal printhead or equivalent linear array technology, when combined with appropriate data compression, is the very high speed with which, compared to galvanometer output, a large volume of ECG data can be graphically presented. One minute of diagnostic high resolution galvanometer recorded ECG data takes one minute to plot;

with the invention here described, the time to plot a minute of compressed ECG data can be significantly less than one second.

SUMMARY OF THE INVENTION

Given the shortcomings of the prior art in defining an acceptable economical "mini-ECG" unit, it is an object of this invention to provide a miniature ECG tracing system wherein, utilizing conventional linear dot array printer technology, ECG tracings can be made in compressed form to allow diagnosis of arrhythmias by a diagnostician.

Yet another object of this invention is to provide a miniature ECG recording system that utilizes thermal print heads of low resolution, for example, those used as computer output devices and plot ECG traces perpendicular to movement of the paper.

A still further object of the device is to provide a system for the printing of a long duration analog wave form utilizing analog to digital conversion and then providing stored values to a linear array of print elements in a timed relationship such that recording of such long duration data is divided into a number of parallel tracks of uniform time duration and plotted with the ECG wave time axis perpendicular to the axis of paper movement.

These and other objects of this invention are achieved in a recorder for printing for example one hour of ECG waveforms utilizing sixty parallel tracks of one minute each or, for example, a one-half hour ECG record in 60 parallel 30 second tracks. In either case recording occurs on a single sheet of (for example) $8\frac{1}{2}'' \times 11''$ paper or on portions of a roll of indefinite length. Such is accomplished by utilizing the large number of printing elements available on a linear dot array printhead. Specifically, ECG data in analog form is obtained utilizing conventional sensors followed by A/D conversion and the storage of the thus generated digital values. The stored values are further processed and the result gated appropriately in time to a linear array of fixed printing elements, for example a linear dot array printhead operated for parallel output in a timed relationship with a chart feed moving perpendicular to the linear array. The activation of a particular print element in the array is a function of the maximum and minimum ECG sample values occurring within the ECG time interval corresponding to the position of that print element within the linear array. The beginning and end of the period of energizing a particular print element, by virtue of the timed relationship of the print commands to the chart feed, provides a line along the direction of the chart motion which, in length and position, represents the spread of values of the pair of ECG samples from which the activation information for that print element is derived.

As described herein, an ECG wave may be sampled in a process of analog to digital (A/D) conversion at a sampling rate of k samples per second. If a linear dot array printhead of effective width L, composed of a total of N print elements, is employed for printing a compressed ECG wave of total duration T seconds across a width $x \leq L$ of a recording medium moving perpendicular to the axis of the array, the total ECG samples to provide one line across the page $= kT$, and the average number of samples represented by each print element $= kT \div N(x/L) = (kTL/Nx)$. Each print element in length x must therefore display information derived from $(kTL/Nx)$ samples. For example, using representative values $k=100$, $N=800$, and $L=8$ inches, consider depicting $T=60$ seconds of ECG waveform information across an $x=7.5$ inch wide portion of a page of recording medium. (The remaining $\frac{1}{2}$ inch of print elements can be used for marginal alphanumeric notation.) In this example, each print element must appropriately represent data from 8 samples of the ECG wave train.

This invention provides means for A/D conversion of an analog ECG wave train, for segregating successive groups of samples, for determining the maximum and minimum sample values for each group, and for serially storing in a memory the values of the max-min pair associated with each group and thus with each print element. When the memory is filled (i.e. all ECG print elements have assigned pair values), the stored data is "read out" effectively in parallel by activating and de-activating the print elements as a function of their associated stored max-min pair values and of the position of the mechanical drive that moves the recording medium across the linear printhead array. Thus a long duration train of heart cycle electrical waveforms is recorded as a succession of short parallel lines transverse to the axis of the printhead; the aggregate of the transverse lines represents with low resolution the basic timing and amplitude information of the input long-duration high resolution waveform train.

In accordance with the present invention, the maximum and minimum amplitudes may be modified to prevent recording gaps which may exist.

This invention will be described in greater detail by referring to the attached drawings and the description of the preferred embodiment that follows.

BRIEF DESCRIPTION OF THE DRAWINGS

FIGS. 2A-2E illustrate signal processing of input ECG signals in accordance with the present invention;

FIG. 3 illustrates the technique of modifying amplitudes to prevent recording gaps;

FIG. 4 illustrates two cases where gaps occur in data recording.

DESCRIPTION OF THE PREFERRED EMBODIMENT

Figure 1:
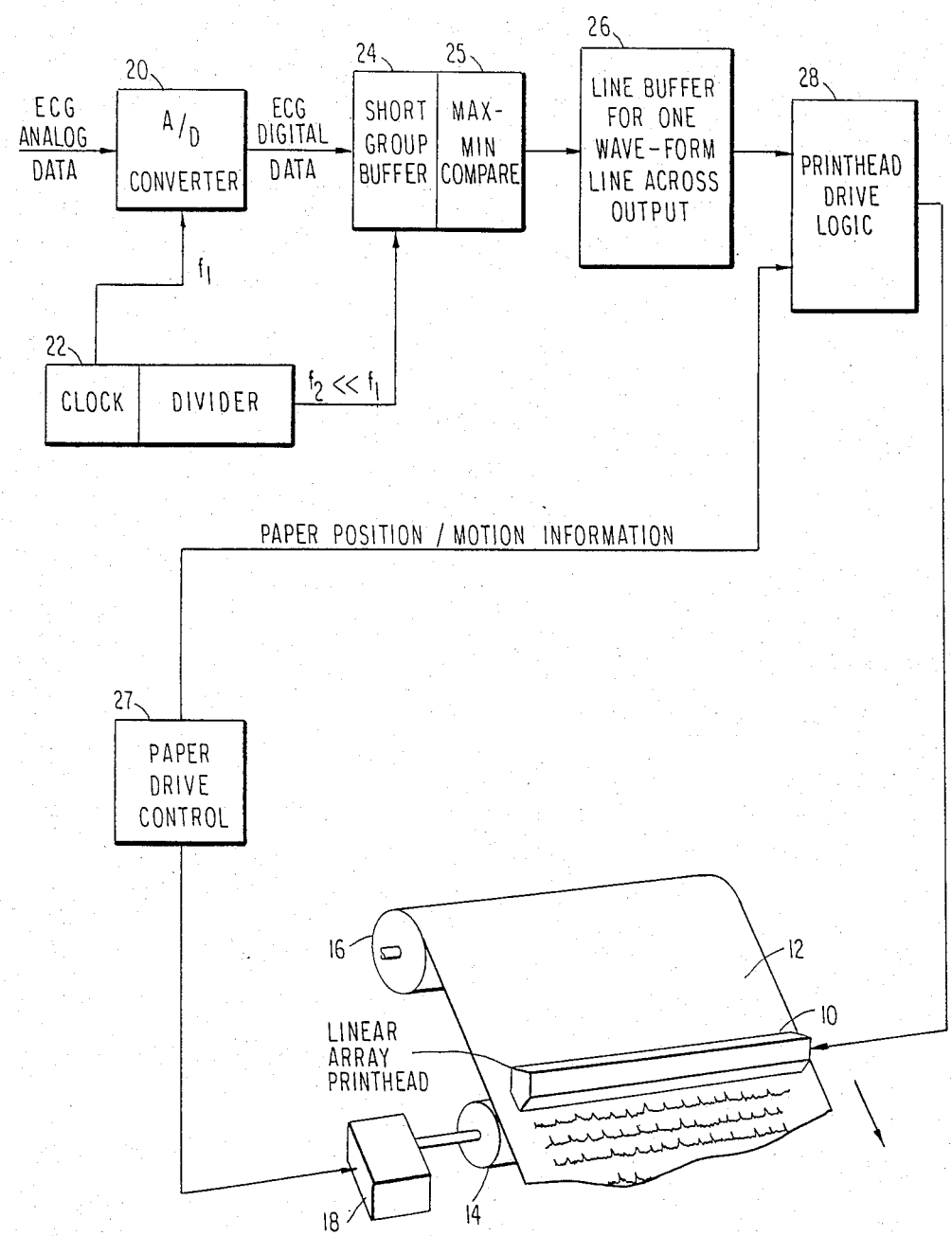
FIG. 1 is a schematic drawing showing the essential elements of this invention.

Referring now to FIG. 1, the overall system, in accordance with the present invention is illustrated. The present invention utilizes a thermal print head 10, for example a linear dot array printer, of the type sometimes used as a computer output printer. The linear array thermal printer 10 has a number of elements N, typically 100 per linear inch, and by selective energizing of elements a thermally sensitive paper 12 is provided with an array of dots to provide a visual record of the data to be recorded. Such linear array printers are well known in the technology. Typically, a platen 14 is disposed below the paper 12 to provide a backing for the thermal print head to achieve uniform contact of the print elements to the paper. The paper 12 is fed from a roll 16 and is driven in a direction of the arrow shown in FIG. 1 in any conventional manner, for example, by pressure rollers, movement of the platen 14, sprockets or the like.

In accordance with this known technology, as any element of the printhead is electrically actuated, a visible dot is formed on the thermal paper. If the same element is repeatedly actuated, the summation of printed dots forms a line or bar placed parallel to the direction of paper travel, that is in the direction of paper movement. The present invention uses the advantages of this conventional technology, a large number of individually activated print elements in a linear array, to print a miniature ECG at a resolution that is low but yet sufficient to allow for diagnosis of arrhythmias. The present invention employs this known technology to construct a compressed ECG. If, for example, the width of the paper 12 is a standard $8\frac{1}{2}'' \times 11''$ page, one hour of ambulatory ECG recording can be accomplished requiring 60 lines each representing one minute of ECG data. The amount of "fan-fold" or roll paper paper that would be required for the same recording at the normal diagnostic 25 mm/sec rate is quite large by comparison (about 90 meters).

A typical currently available thermal linear array printhead utilizes approximately 800 elements within an 8 inch width, thus achieving a density of 100 elements/inch. If, for example, one minute of data were to be printed on the line having 800 elements, this would utilize an average of 13.33 print elements per second of ECG data. The resulting resolution is below that conventionally used to represent and plot data (100-500 samples/sec as set forth in U.S. Pat. No. 4,090,505).

However, in accordance with the present invention, an acceptable mini-ECG may be generated utilizing this small linear print density by employing available printhead technology. That is, the present invention does not require galvanometers of extreme accuracy to drive movable stylii as in conventional diagnostic ECG recording.

Referring to FIG. 2A, consider first an input continuous analog ECG signal and an array of samples shown in FIG. 2A. Each dot represents a discrete sampling point derived from the waveform of FIG. 2A. FIG. 2B denotes time intervals each representing the time span allocated to an individual printhead element of the linear array printhead 10. Successive intervals shown in FIG. 2B therefore correspond to successive groups of samples shown by the dots in FIG. 2A. It will be appreciated that there may be many samples contained in each interval.

FIG. 2C represents a plot wherein for each interval maximum and minimum samples are retained. Thus, as shown in FIG. 2C within those intervals having samples at a single level only, one point is retained since the maximum and minimum values are the same. Within those intervals during which the input signal changes, two sample points are retained. For example, within the positive spike shown in FIG. 2A the retained sampling points are both positive. However, in the case of the transition negative spike shown in FIG. 2A, the sampling points are a positive point and a negative point respectively. The values of the pairs of maximum and minimum points shown in 2C are used to activate each element of the printhead 10 to produce a series of vertical bars which will represent the ECG. Successive lines are printed as data conversion continues; thus on a standard piece of paper, a significant amount of ECG data can be collected. The series of bars generated from the data of FIG. 2C is shown in FIG. 2D. It is understood that linear array printheads do not make solid bars but rather a sequence of closely spaced or overlapping dots would be printed to represent or form a solid line. Thus, while a linear array thermal printer is chosen by way of example, many different types of linear array or other printers may be employed.

FIG. 2E represents a portion of a mini-ECG generated utilizing the method disclosed relative to FIGS. 2A–2D and plotted with a more realistically compressed time axis. It is understood that at a printing density of 100 elements/inch the bars would appear to be touching, thereby defining a transverse waveform. Such an ECG is suitable for arrhythmia diagnosis from an ambulatory ECG, that is one taken over a long duration of time from a patient under study as that individual goes about his daily activities.

Referring back to FIG. 1, the apparatus for sampling and recording input ECG data is illustrated. As is well known, ECG data provides an analog input with generally five distinct waveform portions produced during each normal heart cycle. FIG. 1 portrays a system for printing a wave train composed of many successive heart cycles on each line across the page. Input data is first subjected to analog to digital conversion in converter 20. The clock 22 provides the conversion frequency rate input, an f1. The thus converted digital data is then partitioned by the circuits of the short group buffer 24 at a uniform rate f2 into sequential groups of values that are then processed by the circuits of the max-min compare 25 to select the maximum and minimum value pair for each group; that is data fills the short group buffer 24 in an amount corresponding to the number of dots shown in FIG. 2A for a time interval defined between the partitions shown in FIG. 2B. The resultant pairs of maximum and minimum sample points are then held in line buffer memory 26. It is appreciated that the line buffer memory 26 will store data pairs equal to the number of elements to be actuated in the printhead 10. Thus, if 800 elements are to be actuated for an 8" print width on a standard $8\frac{1}{2}'' \times 11''$ sheet of paper, memory 26 will store 800 data pairs representing maximum and minimum samples, one pair of samples for each of the elements. The stored values are then processed by printhead drive logic 28 to time appropriately the on and off periods of the individual thermal print elements, coordinated in time with the paper motion controlling circuits 27 and mechanical drive mechanism 18. Each of the print elements of printhead 10 will print a bar of length and position on the page that is a function of stored maximum and minimum values. It will be appreciated that each of the elements shown in FIG. 1 comprise devices commercially available that are capable of integration into the described system.

Given the fact that bars are generated as shown in FIG. 2D and that rapid changing of signal levels may occur in some waveform regions, gaps may appear between the bar representations of the signal. That is, a zone may exist where there is no overlap between successive bars. Such is shown in FIG. 3.

FIG. 3 represents an overlay showing the sampling points of FIG. 2A as a result of A/D conversion of an analog ECG input. The bars shown in FIG. 3 represent those which would be printed as a result of maximum and minimum samples obtained within two adjacent intervals. The individual sample points are also shown in FIG. 3. As shown, during areas of rapidly changing signals, a gap may exist between successive bars that would be printed thereby resulting in a gap of the printed ECG. In accordance with the present invention, such recording gaps can be prevented.

Referring to FIG. 4, let $T_1$ = the maximum sample value in a first partition and $B_1$ = the minimum sample value in a first partition. Likewise, for a second, or subsequent partition, let $T_2$ = the maximum value in that partition and $B_2$ = the minimum value in that partition. FIG. 4 shows two cases. In the first, a gap exists since the minimum value $B_1$ is greater than the maximum value $T_2$. In the second case, the maximum value of $T_1$ is less than the minimum value of $B_2$, thereby resulting in a gap.

If, as in Case I, $T_2 > B_1$, then replace the value of $T_2$ with that of $B_1$. If, as in Case II, $B_2 > T_1$, then replace the value of $B_2$ with $T_1$. With these substitutions, as necessary, the bars are drawn as previously described. The effect is to smooth those transition points and eliminate any gaps which may exist.

A further advantage of the present invention is that the same linear array printhead can be used to print alphanumeric characters on the data sheet 12. Consequently, by utilizing any suitable drive and character generator logic, well known in the technology, annotations can be added to the illustrated mini ECG to provide various descriptor data, such as patient name, patient number, date and the like.

Thus, as described herein, the present invention provides parallel plotting of miniature ECG wave trains for significant data compression of the input analog ECG wave sequences. The entire ECG wave train is plotted in parallel with the ECG time axis at right angles to the paper motion. This orientation is therefore orthogonal to that used in most diagnostic ECG plotting systems wherein the paper motion axis is used as the ECG time axis.

It is apparent that modifications of this invention may be practiced without departing from the essential scope of this invention. For example, while one circuit for printing a single line has been illustrated, it is apparent that a second parallel memory may be employed to store a second line of data. Thus, the memories may be alternately loaded and read out in correspondence with the advance rate of the recording medium. Simple gating would be employed.

Also, different printers may be employed so long as sufficient print element density is maintained.

Moreover, while data compression on the order of one minute of ECG data/line has been described, it is apparent that other degrees of compression per printed line can be utilized.

We claim:

1. A method of printing an analog waveform having a time variable comprising the steps of:
converting said analog waveform into a time sequence of digitally expressed values;
forming predetermined groups of said digital data and determining maximum and minimum amplitude values of said digital data within said groups;
serially storing said maximum and minimum values;
moving a recording medium past a transversely oriented linear array of discrete recording elements; and
reading out in parallel in accordance with said serial stored values to said recording elements and actuating respective elements in parallel by said stored values at initial times and for time durations for each element that is a function of the stored maximum and minimum amplitude values for that element, wherein said waveform is recorded as a series of appropriately placed short parallel longitudinal lines to form in aggregate a transverse waveform display on said recording medium.

2. The method of claim 1 wherein said analog waveform is an ECG.

3. The method of claim 1 wherein said predetermined groups are determined as a function of the time duration to be printed on a single line and the number of recording elements to print said line.

4. The method of claim 1 further comprising the steps of determining the existence of a lack of overlap between successive longitudinal lines of data and, modifying the stored values to eliminate said lack of overlap.

5. The method of claim 4 wherein if the stored minimum value of one data group is greater than the stored maximum value of a succeeding data group, the stored minimum value in said one data group is used as the stored maximum value in said succeeding data group.

6. The method of claim 4 wherein if the stored maximum value of one data group is less than the stored minimum value in a succeeding data group, the value of the stored maximum value in said one data group is used as the stored minimum value in said succeeding data group.

7. The method of claim 1 further comprising repeating the steps of forming second predetermined groups of data, determining second serial paired max-min stored values, and reading out said second serial stored values in an alternate cycle with said previous serial stored values to print successive transverse lines of data.

8. The method of claim 1 further comprising the step of moving said recording medium at a uniform average speed perpendicular to said linear array.

9. A method of plotting an ECG comprising the steps of dividing digitized ECG data into predetermined groups of data and plotting data derived from said groups as short adjacent linear segments having in the aggregate a direction representative of ECG time wherein said adjacent linear segments define a waveform train across a data recording medium running perpendicular to said waveform train time axis.

10. The method of claim 9 wherein the data plotted for each group is a line connecting points that are spatially related to the maximum and minimum amplitudes of ECG data within said predetermined group of data.

11. The method of claim 9 further comprising the step of converting analog ECG data into digital ECG data and dividing said digital ECG data into groups having a predetermined member of samples within each group.

12. The method of claim 11 wherein said predetermined number of samples is a function of the member of waveform lines to be printed representing a given time duration of ECG data.

13. The method of claim 9 further comprising the steps altering said ECG data in said predetermined groups to print with an overlap between adjacent printhead element lines.

* * * * *